US00PP31107P3

(12) United States Plant Patent
Velazquez

(10) Patent No.: US PP31,107 P3
(45) Date of Patent: Nov. 26, 2019

(54) ***PRUNUS* PLANT NAMED 'MONARONE'**

(50) Latin Name: *Prunus laurocerasus*
Varietal Denomination: MONARONE

(71) Applicant: Cesar Velazquez, Salem, OR (US)

(72) Inventor: Cesar Velazquez, Salem, OR (US)

(73) Assignee: Monrovia Nursery Company, Azusa, CA (US)

( * ) Notice: Subject to any disclaimer, the term of this patent is extended or adjusted under 35 U.S.C. 154(b) by 18 days.

(21) Appl. No.: 15/731,677

(22) Filed: Jul. 13, 2017

(65) Prior Publication Data

US 2019/0021194 P1 Jan. 17, 2019

(51) Int. Cl.
*A01H 5/12* (2018.01)
*A01H 6/74* (2018.01)

(52) U.S. Cl.
USPC ..... Plt./180
CPC ..... *A01H 6/7427* (2018.05)

(58) Field of Classification Search
USPC ..... Plt./180, 226
See application file for complete search history.

*Primary Examiner* — Anne Marie Grunberg
(74) *Attorney, Agent, or Firm* — Cassandra Bright

(57) ABSTRACT

A new and distinct cultivar of *Prunus* plant named 'MONARONE' is disclosed, characterized by reduced flower and fruit production on compact plants. Foliage is distinctively short and has less susceptibility to shot hole disease. The new cultivar is a *Prunus*, suitable for ornamental garden purposes.

2 Drawing Sheets

Latin name of the genus and species: *Prunus laurocerasus*.

Variety denomination: 'MONARONE'.

BACKGROUND OF THE INVENTION

The new cultivar is a product of a chance discovery in a commercial setting by the inventor. In Summer 2013, the inventor, Cesar Velazquez discovered an interesting whole plant mutation in a commercial planting of the unpatented parent variety *Prunus laurocerasus* 'Majestic Jade'. This mutation was discovered at a commercial nursery in Dayton, Oreg.

During the summer of 2013 the inventor propagated the interesting mutation by semi-softwood cuttings at the commercial nursery in Dayton, Oreg. The initial propagation showed the mutation to be stable and additional generations were propagated, also by semi-hardwood cuttings. Approximately 3 generations have been reproduced since 2013, and have shown that the unique features of this cultivar are stable and reproduced true to type.

SUMMARY OF THE INVENTION

The cultivar 'MONARONE' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MONARONE' These characteristics in combination distinguish 'MONARONE' as a new and distinct *Prunus* cultivar:

1. More compact plant habit.
2. Shorter foliage than typical.
3. Reduced flower and fruit production.

4. Reduced susceptibility to shot hole disease (*Xanthomonas pruni* and *X. campestris*).

COMPARISON TO PARENT VARIETY

Plants of the new cultivar 'MONARONE' are similar to plants of the parent; *Prunus laurocerasus* 'Majestic Jade' in most horticultural characteristics, however, plants of the new cultivar 'MONARONE' differ from the parent variety in the following:

1. More compact plant habit.
2. Shorter foliage.
3. Less flowers and fruit produced.
4. Less susceptible to leaf shot disease (*Xanthomonas pruni* and *X. campestris*).

COMMERCIAL COMPARISON

'MONARONE' can be compared to the commercial variety *Prunus laurocerasus* 'Nana', unpatented. Plants of the new cultivar 'MONARONE' are similar to plants of 'Nana' in most horticultural characteristics, however, plants of the new cultivar 'MONARONE' differ in the following:

1. Darker green foliage.
2. Less flower and fruit production
3. Cold tolerant to USDA Zones 6-9, 'Nana' tolerates temperatures in USDA Zones 7-9.

BRIEF DESCRIPTION OF THE PHOTOGRAPHS

Figure 1:
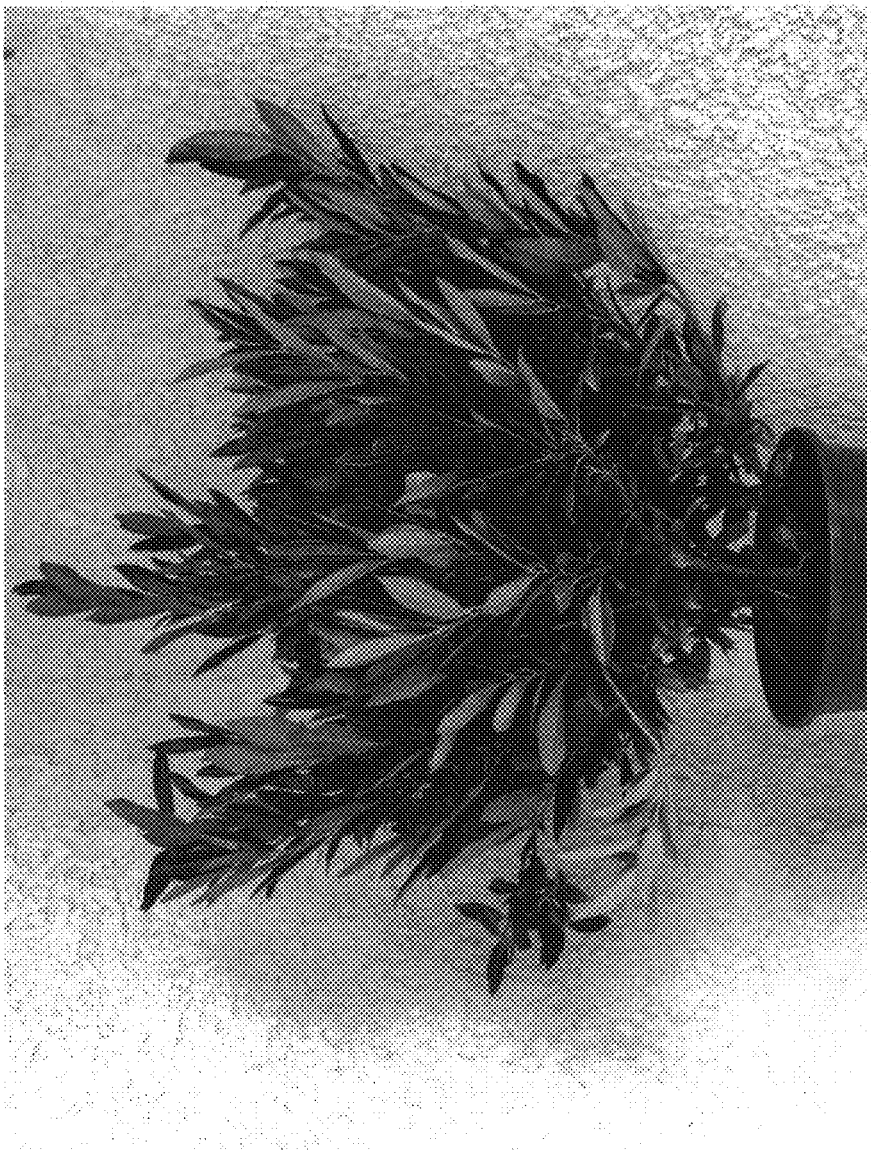

The accompanying photograph in FIG. 1 illustrates in full color a typical plant of 'MONARONE' grown outdoors in Oreg.

Figure 2:
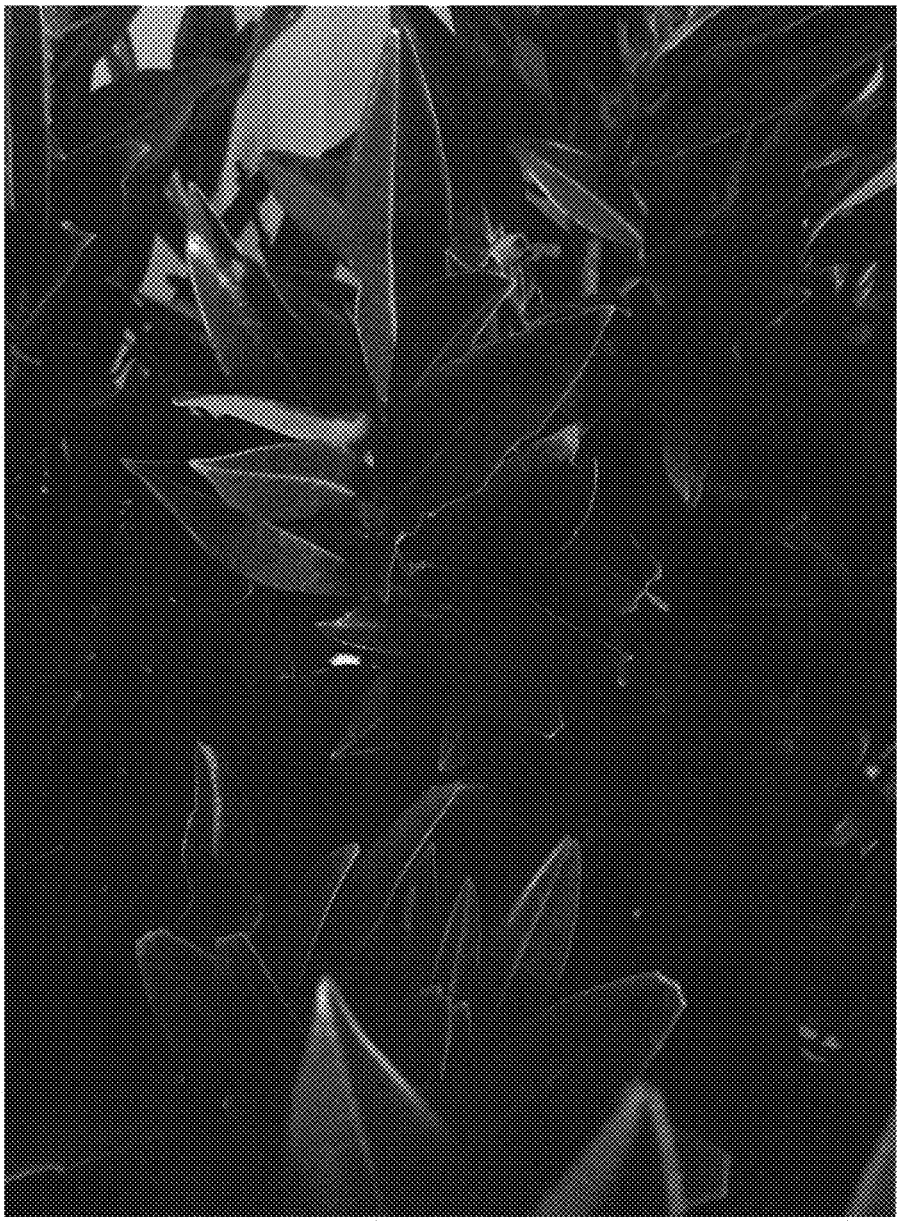

FIG. 2 illustrates in full color a close up of the foliage. The plant is approximately 2 years old, and is planted in a 5 gallon pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'MONARONE' plants grown outdoors in Dayton, Oreg. Plants are approximately 2 to 3 years old, in a 5 gallon nursery container. Temperatures ranged from −8° C. to 20° C. at night to 5° C. to 35° C. during the day. Measurements and numerical values represent averages of typical plant types.

Botanical classification: *Prunus laurocerasus* 'MONARONE'.

PROPAGATION

Time to rooting: Approximately 4 to 8 weeks at approximately 20° C. to 30° C. from semi-hardwood cuttings.

Root description: Fine, fibrous young roots. Older roots becoming woody. Tan and brown in color, not accurately measured with R.H.S. chart.

PLANT

Growth habit: Upright and outwardly spreading evergreen shrub. Moderately dense.

Shape: Round.

Height: Approximately 60 to 65 cm.

Plant spread: Approximately 60 to 65 cm.

Branching characteristics: Above average branching for the species, average 6 to 8 main branches, angled approximately 15 to 45 degrees on average.

Length of lateral branches: Approximately 25 to 40 cm.

Diameter of lateral branches: Approximately 0.7 to 1.0 cm.

Lateral branch strength: Very strong, with some flexibility.

Lateral branch color: Young branches near RHS Yellow-Green 144A. Mature branches: Near RHS Greyed-Green 197A.

Stem texture: No pubescence observed. Texture moderately rough, somewhat scaly. Lenticels: Scant, round, 1mm diameter colored near 197D. Occuring only on older, woody branches.

Number of leaves per lateral branch: Average 25 to 45.

Internode length: 1.0 to 1.5 cm.

Age of plant described: Approximately 2 to 3 years.

FOLIAGE

Leaf:

- *Type*.—Simple.
- *Arrangement*.—Alternate.
- *Average length*.—Approximately 8.0 to 10.5 cm.
- *Average width*.—Approximately 2.0 to 2.5 cm.
- *Shape of blade*.—Elliptic.
- *Apex*.—Acute.
- *Base*.—Attenuate.
- *Attachment*.—Short petiolate.
- *Margin*.—Entire.
- *Aspect*.—Moderate upward fold from center vein.
- *Texture of top surface*.—Smooth.
- *Texture of bottom surface*.—Smooth.
- *Appearance of top surface*.—Very glossy.
- *Texture of bottom surface*.—Matte.
- *Leaf internode length*.—Approximately 0.5 to 1.1 cm.
- *Color*.—Young foliage upper side: Near RHS Green 139A. Young foliage under side: Near RHS Green 143C. Mature foliage upper side: Near RHS Green 139A. Mature foliage under side: Near RHS Green 143C.
- *Venation*.—Type: Pinnate. Venation color upper side: Near Green 143C. Venation color under side: Near RHS Yellow-Green 144B.

Petiole:

- *Length*.—6 mm.
- *Width*.—3 mm.
- *Texture*.—Glabrous all surfaces.
- *Color*.—Upper Surface: Yellow-Green 144B. Lower Surface: Yellow Green 144A.

FLOWER

Inflorescence:

- *Description*.—Single flowers arranged in racemes.
- *Flowering season*.—Spring.
- *Flower longevity*.—3-4 weeks.
- *Fragrance*.—Moderate to strong.
- *Inflorescence per branch*.—Average range 1 to 5.
- *Number of flowers per inflorescence*.—About 100 to 150.
- *Inflorescence height*.—Avg. 8.0 cm.
- *Inflorescence diameter*.—Avg. 5.0 cm.

Flowers:

- *Flower diameter*.—6 mm.
- *Flower depth*.—5 mm.
- *Flower angle*.—Outwardly facing.
- *Persistent of self-cleaning*.—Self-Cleaning.
- *Flower bud*.—Length: 3 mm. Diameter: 2 mm. Shape: Round. Color: White 155A.
- *Petals*.—Number: 5. Arrangement: Whorl. Length: Avg. 4 mm. Width: Avg. 2.5 mm. Shape: Obovate. Apex: Obtuse. Base: Fused. Margin: Entire. Texture: Glabrous, silky upper and lower surfaces. Color: Immature upper surface: White 155A. Immature lower surface: White 155A. Mature upper surface: Yellow-White 158D. Mature lower surface: White 155A.

Hypanthium:

- *Diameter*.—4 mm.
- *Length*.—3 mm.
- *Shape*.—Cup-shaped.
- *Color*.—When opening: Upper surface: Near RHS Yellow-White 158D. Lower surface: Near RHS Yellow-White 158D. Fully opened: Upper surface: Near RHS Yellow 13D. Lower surface: Near RHS Yellow 11D.

Calyx/sepals:

- *Quantity per flower*.—Fused into a single, conical structure.
- *Length*.—3 mm.
- *Width*.—3 mm.
- *Margin*.—Entire.
- *Texture*.—Smooth.
- *Color*.—Inner surface: Near RHS Yellow-Green 146C. Outer surface: Near RHS Yellow-Green 146C.

Peduncle:
*Length*.—Avg. 4.5 cm.
*Width*.—Avg. 1.5 mm.
*Color*.—146A.
*Texture*.—Glabrous.
*Angle*.—Upright and slightly outward.
*Strength*.—Strong.
Pedicels:
*Length*.—Avg. 1 mm.
*Diameter*.—Avg. 1 mm.
*Texture*.—Pubescent.
*Color*.—Yellow-Green 146C.
*Strength*.—Strong.

REPRODUCTIVE ORGANS

Gynoecium:
*Pistil number*.—1.
*Pistil length*.—Less than 1 mm.
*Stigma shape*.—Disc.
*Stigma color*.—Yellow-White 158D.
*Style length*.—Less than 1 mm.
*Style color*.—White 155D.
Androecium:
*Stamen number*.—5.
*Filament length*.—1 mm.
*Filament color*.—Yellow-White 158D.
*Anther shape*.—Oblong.
*Anther length*.—0.5 mm.
*Anther color*.—Yellow 6 B.
*Amount of pollen*.—Scant.
*Pollen color*.—Yellow 6B.

OTHER CHARACTERISTICS

Fruit: Approximately 5 to 20 per inflorescence. Spherical drupe 4 mm long, 4 mm in diameter, colored Black 202A over entire fruit, smooth texture, lenticels not observed. Fruits are slightly asymmetric and circular in lateral view. Fruit base is slightly depressed. Fruit apex is slightly and shallowly depressed. Interior cavity of the fruit is solid, somewhat dry and without observed stone. Fruit pedicel about 3 mm long on a fruit rachis of between 1.5 to 4.5 cm. Pedicel and fruit rachis colored near Yellow-Green 145C. Self-fruitful. Fruit production is erratic, occurring between July and September, some years no fruit may bear. Spurs not observed present.

Disease and pest resistance: Observed less susceptible to the leaf blight referred to as "shot hole" disease: (*Xanthomonas pruni* and *X. campestris*). Less leaf damage, in the form of small holes in the leaf, have been observed than in comparable varieties grown in identical conditions.

Drought tolerance: No tolerance for drought, extra water required in extremely high temperatures.

Temperature tolerance: USDA Zones 6 to 9.

What is claimed is:

1. A new and distinct cultivar of *Prunus laurocerasus* plant named 'MONARONE' as herein illustrated and described.

* * * * *